(12) United States Patent
Tsujii

(10) Patent No.: US 7,039,151 B2
(45) Date of Patent: May 2, 2006

(54) RADIOGRAPHIC IMAGE PROCESSING METHOD AND RADIATION IMAGING DEVICE

(75) Inventor: Osamu Tsujii, Tochigi (JP)

(73) Assignee: Canon Kabushiki Kaisha, Tokyo (JP)

( * ) Notice: Subject to any disclaimer, the term of this patent is extended or adjusted under 35 U.S.C. 154(b) by 36 days.

(21) Appl. No.: 10/829,738

(22) Filed: Apr. 21, 2004

(65) Prior Publication Data

US 2004/0223583 A1   Nov. 11, 2004

(30) Foreign Application Priority Data

May 7, 2003   (JP)   ............... 2003-129453

(51) Int. Cl.
*G21K 1/00* (2006.01)
*A61B 6/00* (2006.01)

(52) U.S. Cl. .................. 378/7; 378/19; 378/4; 378/154

(58) Field of Classification Search .................... 378/4, 378/7, 19, 86, 98.4, 98.8, 154, 155, 62, 186, 378/15, 207, 901
See application file for complete search history.

(56) References Cited

U.S. PATENT DOCUMENTS

| 4,866,744 | A | * | 9/1989 | Yoshida | .......................... | 378/7 |
| 6,041,097 | A | * | 3/2000 | Roos et al. | ................... | 378/62 |
| 6,480,574 | B1 | * | 11/2002 | Goto | ........................... | 378/154 |
| 6,707,884 | B1 | * | 3/2004 | Ogawa | ........................ | 378/154 |
| 6,850,597 | B1 | * | 2/2005 | Matsumoto et al. | ........ | 378/154 |
| 2001/0033638 | A1 | * | 10/2001 | Inoue | .......................... | 378/154 |

FOREIGN PATENT DOCUMENTS

| JP | 2000-107162 | 4/2000 |
| JP | 2000-157530 | 6/2000 |
| JP | 2001-188096 | 7/2001 |
| JP | 2001-212139 | 8/2001 |
| JP | 2002-325765 | 11/2002 |

OTHER PUBLICATIONS

English Abstract of JP 2000-107162 (Item A).
English Abstract of JP 2000-157530 (Item B).
English Abstract of JP 2001-188096 (Item C).
English Abstract of JP 2001-212139 (Item D).
English Abstract of JP 2002-325765 (Item E).

* cited by examiner

*Primary Examiner*—Edward J. Qlick
*Assistant Examiner*—Irakli Kiknadze
(74) *Attorney, Agent, or Firm*—Morgan & Finnegan, LLP

(57) ABSTRACT

A radiation imaging device includes a radiation source which rotates around a subject to be examined and irradiates the subject with radiation, a two-dimensional detector in which a plurality of detection elements for detecting radiation from the radiation source are two-dimensionally arranged, and a grid which is placed in front of the two-dimensional detector to remove scattered radiation of the radiation. This device performs computation with respect to a subject image obtained by the two-dimensional detector by using the subject image and a gain image obtained by the two-dimensional detector, and executes removal of a grid pattern due to the grid and gain correction. The device reconstructs an image on the basis of the subject image obtained using the subject image from which a grid pattern due to the grid is removed and which is gain-corrected.

8 Claims, 7 Drawing Sheets

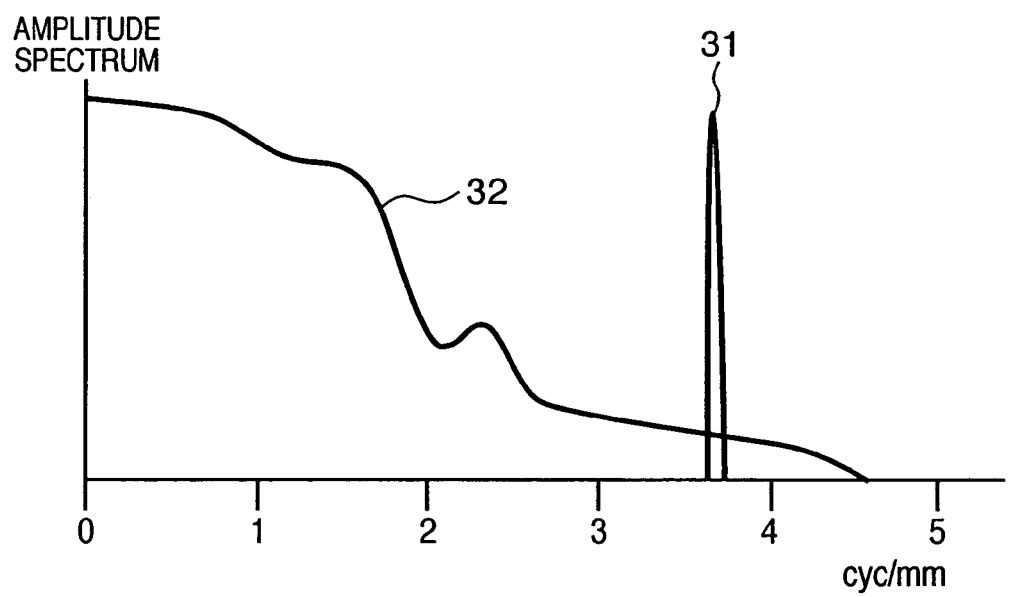
F I G. 7A
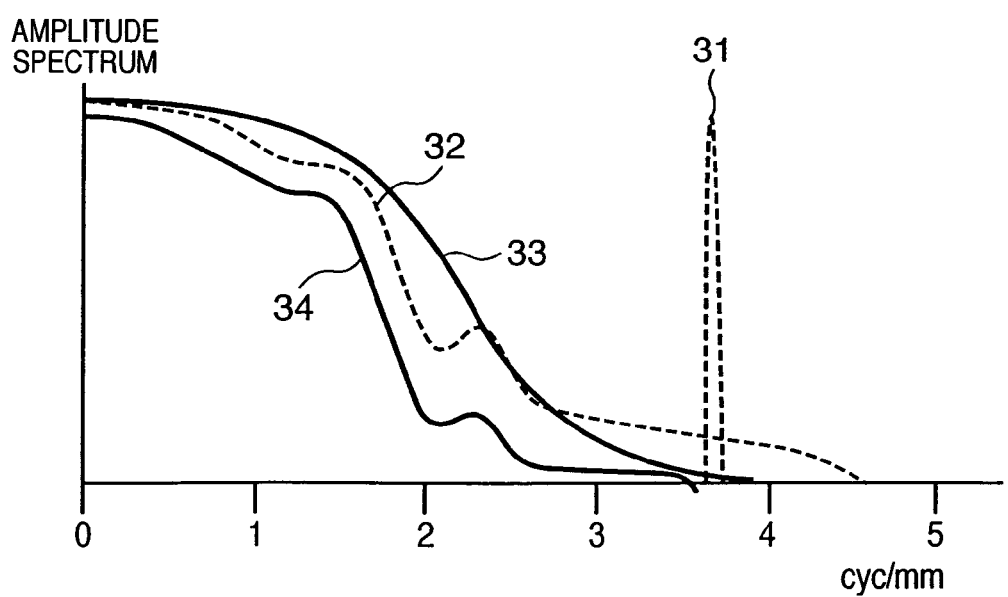
F I G. 7B

RADIOGRAPHIC IMAGE PROCESSING METHOD AND RADIATION IMAGING DEVICE

FIELD OF THE INVENTION

The present invention relates to a radiation imaging device which performs CT (Computed Tomography) imaging by using radiation such as X-rays.

BACKGROUND OF THE INVENTION

A conventional X-ray CT device has been known, which irradiates a subject to be examined with X-rays, detects X-rays transmitted through the subject or scattered by the subject with an X-ray detector, and provides a fluoroscopic image, tomogram, or three-dimensional image of the subject on the basis of the X-ray detection output (X-ray photon count).

A cone beam CT device has recently been developed as such an X-ray CT device. A general X-ray CT device uses an X-ray beam formed thin in the Z direction (this beam is a fan beam). In contrast to this, a cone beam CT device uses an X-ray beam which also spreads in the Z direction (this X-ray beam is called a cone beam).

Studies have recently been undertaken to realize a conventional CT device (i.e., having only one row) as this cone beam CT device in the form equivalent to a so-called third-generation type or a scheme called an R/R type. The third-generation type CT is designed to perform scanning (acquisition of projection data) while making a pair of an X-ray source and a detector pivot around a subject to be examined.

FIG. 2 is a view showing an example of a cone beam CT device. The cone beam CT device shown in FIG. 2 belongs to third-generation type CT devices, and makes both an X-ray source and an X-ray detector pivot about the Z-axis around a subject to be examined. They make one rotation to complete scanning of a region of interest. In a general X-ray CT device, detection elements are arranged in one line in a channel (CH) direction for sampling. Each element is identified by a channel number. In contrast to this, in a cone beam CT device, as shown in FIG. 2, detection elements are also arranged in the Z direction (row direction). That is, the detector of the cone beam CT device has detection elements two-dimensionally arranged in the form of an orthogonal lattice. According to such a cone beam CT device, detection elements are arranged in the two directions, i.e., the Z direction (row direction) and CH direction, in the form of a lattice to form a detector, and radiation is applied in the form of a cone by making it have a thickness in the Z direction as well, thereby obtaining projection data corresponding to a plurality of columns at once.

With regard to the above cone beam CT devices, a device using a flat panel detector (to be referred to as an FPD hereinafter) has been expected to be commercialized. Unlike a conventional one-dimensional sensor, an FPD which is a two-dimensional sensor allows interference of scattered radiation. This may cause a decrease in contrast.

In a cone beam CT device, in order to remove scattered radiation, division plates made of lead or tungsten are inserted between the detection elements in the CH direction to separate them from each other, and blades (slits) are inserted between the detection elements to separate them from each other in the Z-axis direction. In X-ray imaging using an FPD, a grid for scattered radiation removal is generally used as disclosed in Japanese Patent Laid-Open No. 2001-212139. The blades are inserted between the detectors to separate them from each other in the Z direction. That is, the detector pitch in the Z direction is equal to the blade pitch. On the other hand, the grid is placed in front of the detectors, and hence may shield the detectors. This causes a shadow on an image.

Japanese Patent Laid-Open No. 2000-107162 discloses a technique of inserting a plurality of blades, which are inserted in the Z-axis direction to remove scattered radiation, between the respective detection elements for separation in the Z-axis direction. This reference also discloses a technique of moving a plurality of blade modules arranged in the Z direction over the detectors of a fourth-generation CT (a CT device having detectors arranged in the form of a ring in the CH direction).

Japanese Patent Laid-Open No. 2000-157530 discloses a technique in which a grid similar to the one used for X-ray imaging to remove scattered radiation is used in a cone beam CT device. According to Japanese Patent Laid-Open No. 2000-157530, in order to prevent moire in acquired data which is caused when the grid is inserted, the grid is moved in a direction perpendicular to the extending direction of grid elements to prevent any grid image from remaining during X-ray imaging.

Japanese Patent Laid-Open No. 2001-188096 discloses a structure in which lattice-like grooves are formed in the glass substrate of an FPD, and the grooves are filled with an X-ray absorbing material, thereby reducing scattered radiation.

Japanese Patent Laid-Open No. 2001-212139 discloses a technique of performing data processing to reduce grid patterns from an image obtained by X-ray imaging using a fixed grid.

As described above, when a cone beam CT device is to be formed, blades are inserted in the Z-axis direction, as disclosed in Japanese Patent Laid-Open No. 2000-107162. In a cone beam CT device using an FPD, however, it is mechanically difficult to insert blades between the respective detectors in the Z-axis direction, as described in Japanese Patent Laid-Open No. 2000-107162. Such a structure is expensive, even if possible. This is because, when an FPD is used, detection elements corresponding to several hundred channels (CHs) may need to be arranged in the Z-axis direction as well.

As proposed in Japanese Patent Laid-Open No. 2000-157530, therefore, a grid for scattered radiation may be applied to a CT device. However, the grid directly blocks part of X-rays while cutting scattered X-rays. The grid blocks X-rays in accordance with the arrangement of the grid. This generally causes damage to an image in the form of a grid pattern. In CT, since inverse projection is performed in the form of rotation, if a grid pattern remains in an X-ray image, a ring-like false image (artifact) occurs upon image reconstruction. According to Japanese Patent Laid-Open No. 2000-157530, therefore, a grid moving mechanism is provided to move the grid during X-ray imaging to remove a grid shadow from an X-ray image. However, a very special mechanism is required to move the grid in the form of an arc. When the grid is to be moved in the Z-axis direction, the grid must be moved in a direction perpendicular to the direction of rotational motion, resulting in resonance and the like. This technique is therefore impractical.

Although Japanese Patent Laid-Open No. 2001-188096 discloses a two-dimensional radiation detector provided with a lattice-like X-ray absorbing member to remove scattered X-rays, there is no description about an arrangement using an FPD and grid. Although Japanese Patent Laid-Open No. 2001-212139 discloses an X-ray imaging device for simple imaging using an FPD and grid, there is no description about a CT device.

SUMMARY OF THE INVENTION

The present invention has been made in consideration of the above problems, and has as its object to include an arrangement for removing scattered radiation by using a grid fixed to a radiation detector, and effectively suppress the occurrence of artifacts in CT imaging.

In order to achieve the above object, a radiation imaging device according to the present invention has the following arrangement. That is, a radiation imaging device comprises: a radiation source which rotates around a subject to be examined and irradiates the subject with radiation; a two-dimensional detector in which a plurality of detection elements for detecting radiation from the radiation source are two-dimensionally arranged; a grid which is placed in front of the two-dimensional detector to remove scattered radiation of the radiation; a correction unit configured to perform computation with respect to a subject image obtained by the two-dimensional detector by using the subject image and a gain image obtained by the two-dimensional detector, and execute removal of a grid pattern due to the grid and gain correction; and a reconstruction unit configured to reconstruct an image on the basis of the subject image obtained by the correction unit.

In addition, in order to achieve the above object, a control method for a radiation imaging device according to the present invention, there is provided an image processing method in a radiation imaging device including a radiation source which rotates around a subject to be examined and irradiates the subject with radiation, a two-dimensional detector in which a plurality of detection elements for detecting radiation from the radiation source are two-dimensionally arranged, and a grid which is placed in front of the two-dimensional detector to remove scattered radiation of the radiation, comprising: a correction step of performing computation with respect to a subject image obtained by the two-dimensional detector by using the subject image and a gain image obtained by the two-dimensional detector, and executing removal of a grid pattern due to the grid and gain correction; and a reconstruction step of reconstructing an image on the basis of the subject image obtained in the correction step.

Other features and advantages of the present invention will be apparent from the following description taken in conjunction with the accompanying drawings, in which like reference characters designate the same or similar parts throughout the figures thereof.

BRIEF DESCRIPTION OF THE DRAWINGS

The accompanying drawings, which are incorporated in and constitute a part of the specification, illustrate embodiments of the invention and, together with the description, serve to explain the principles of the invention.

FIGS. 7A and 7B are graphs for explaining grid pattern removal processing.

DETAILED DESCRIPTION OF THE PREFERRED EMBODIMENTS

Preferred embodiments of the present invention will now be described in detail in accordance with the accompanying drawings.

<First Embodiment>

Figure 1:
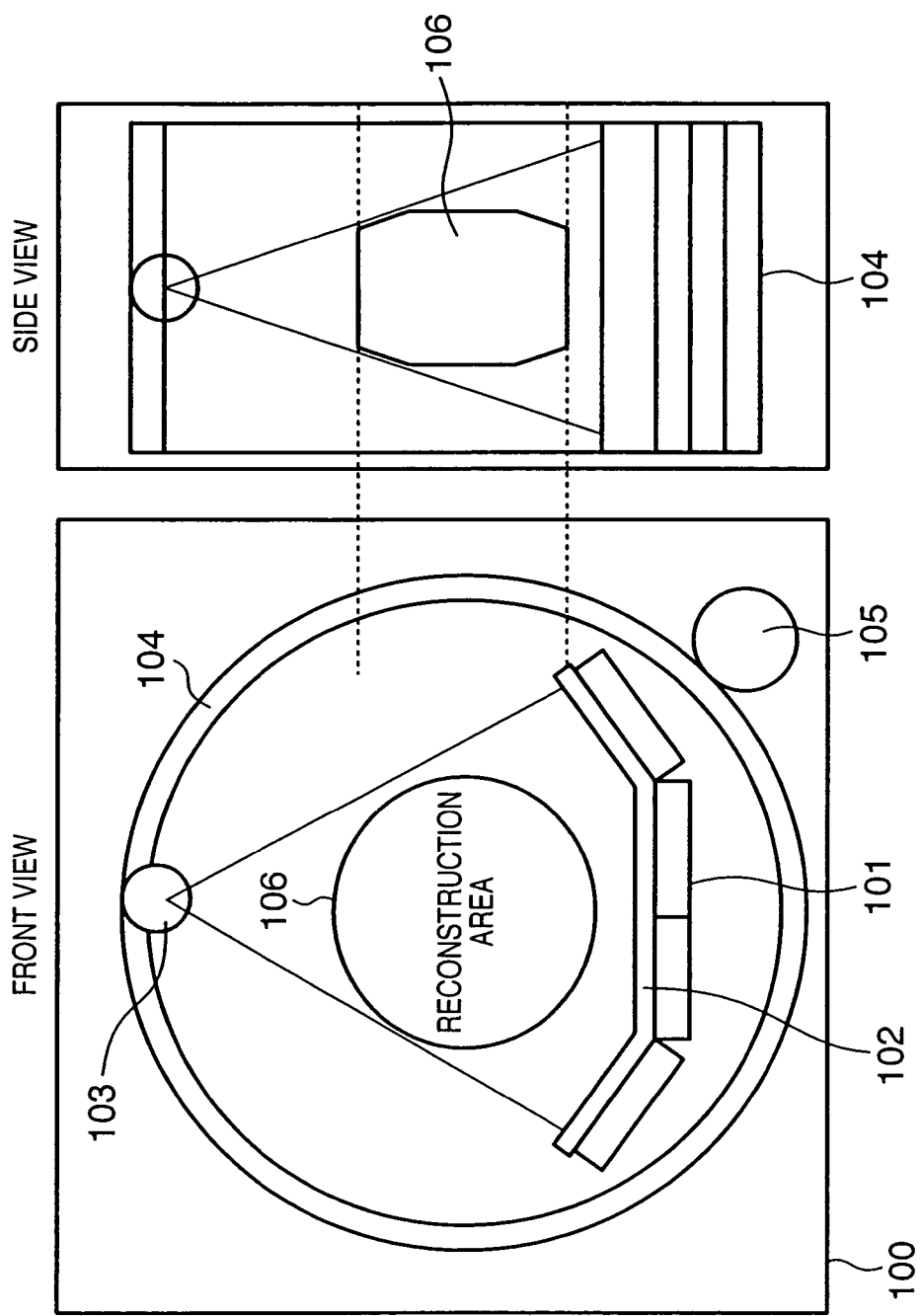
FIG. 1 is a view showing the schematic arrangement of a cone beam CT device according to the first embodiment.

FIG. 1 is a view showing an example of the arrangement of an X-ray CT device according to the first embodiment. An X-ray tube 103 is fixed in a rotating frame 104. An X-ray sensor 101 is placed centered on the focus of the X-ray tube 103. Referring to FIG. 1, the X-ray sensor 101 includes four two-dimensional detectors (FPDs), which are arranged to substantially form an arc. Note, however, that the X-ray sensor 101 may be further divided into smaller parts (e.g., 16 parts), and the divided parts may be arranged in the form of an arc or flat.

A grid 102 for scattered radiation removal is placed in front of (X-ray tube side) of the X-ray sensor 101. The grid 102 reduces scattered radiation from a subject to be examined which is placed in a reconstruction area 106. The grid 102 may be a striped grid used for simple X-ray imaging or a lattice grid having stripes overlapping almost orthogonally. The above arrangement is housed in a gantry 100.

The grid 102 may be either of a focus type or a parallel type. The focus type is designed such that the respective grid elements of the grid 102 are arranged to be inclined toward the focal position. The parallel type is designed such that the respective grid elements are arranged to be parallel to each other. Note that a focus type grid is preferable because of little shading. Obviously, the focal position of a focus type grid coincides with an X-ray focus.

The rotating frame 104 is rotated about the center of the reconstruction area 106 by a rotation gear 105. As shown in a side view of FIG. 1, the X-ray sensor 101 is placed flat in the rotation axis direction. This side view also shows the size of the reconstruction area 106 formed by this imaging system in the Z-axis direction.

Figure 2:
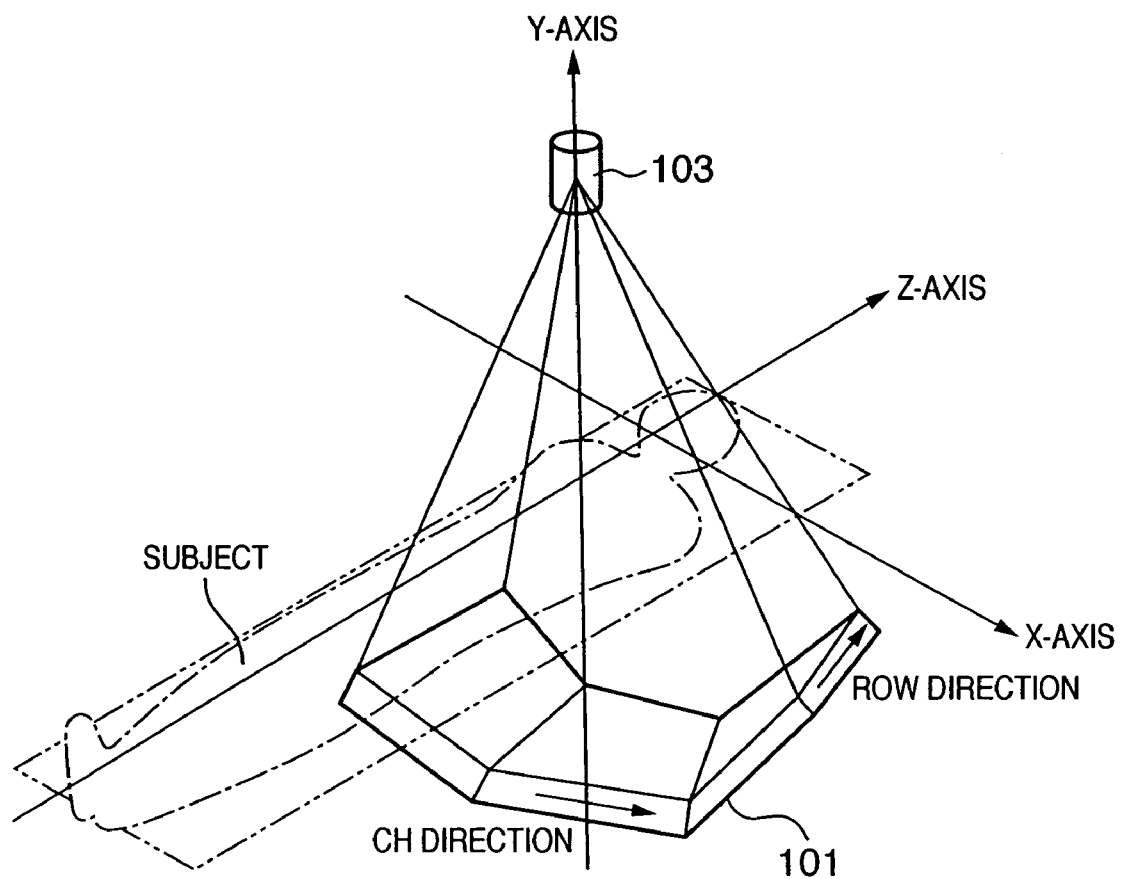
FIG. 2 is a view for explaining a data acquisition coordinate system in the cone beam CT device according to the first embodiment.

FIG. 2 is a view showing the coordinate axes of a data acquisition system in this X-ray CT device. Referring to FIG. 2, the X-ray sensor 101 is comprised of three flat two-dimensional detectors (FPDs), the rotation axis is the Z-axis, the channel (CH) direction is the X-axis, and a line extending from the X-ray focal position to the center of the X-ray sensor 101 is the Y-axis. Note that the arrangement of these coordinate axes is the same when four FPDs are arranged as shown in FIG. 1.

Figure 3:
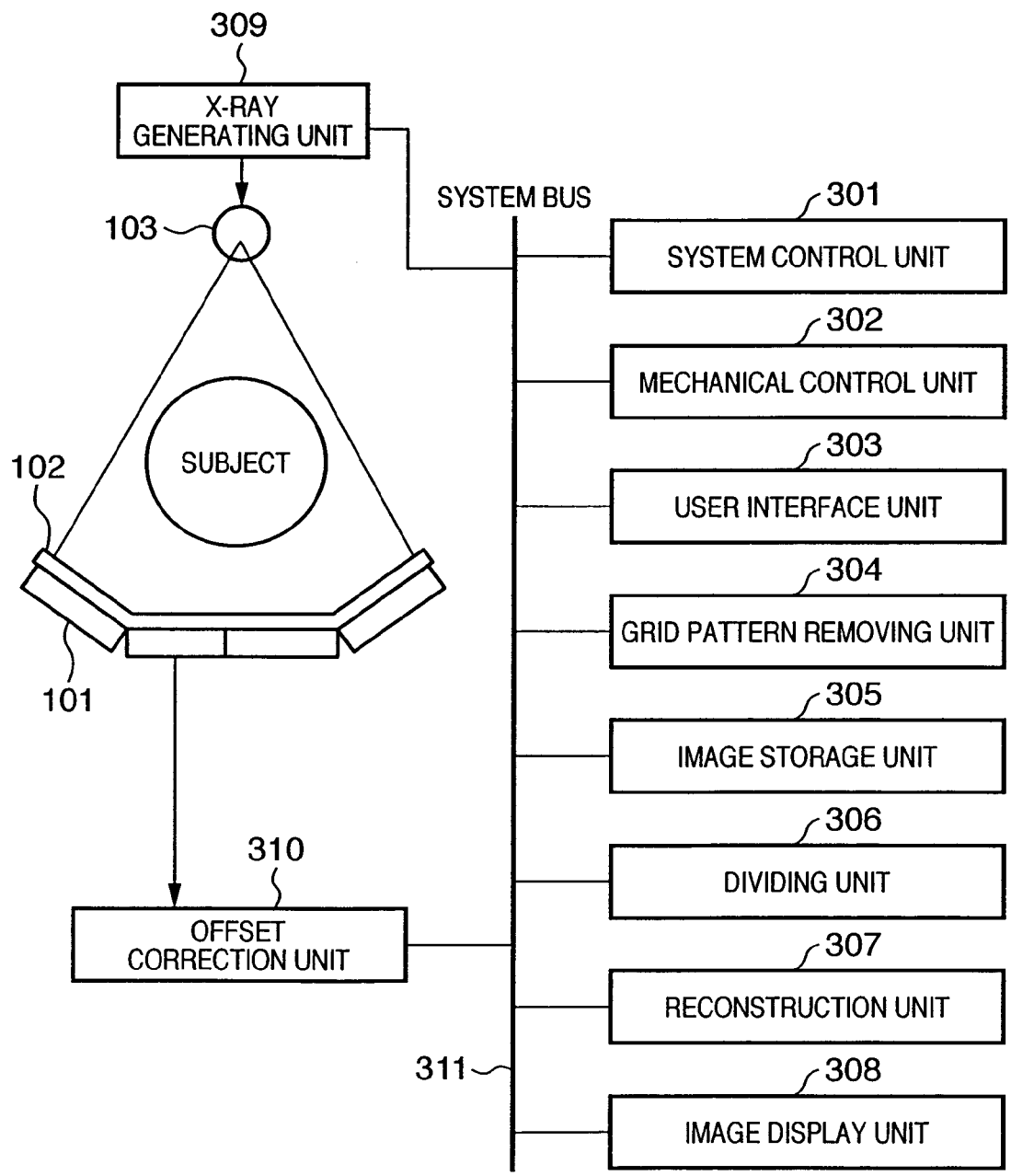
FIG. 3 is a block diagram showing the arrangement of a cone beam CT device according to the first embodiment.

FIG. 3 is a view showing the system arrangement of the X-ray CT device according to the first embodiment. The X-rays emitted from the X-ray tube 103 under the control of an X-ray generating unit 309 are transmitted through a subject to be examined and reach the X-ray sensor 101 while scattered radiation is attenuated by the grid 102 for scattered radiation removable. Note that the grid 102 is preferably inserted parallel to a detection element array (parallel to the CH direction, i.e., parallel to the plane of rotation about the Z-axis) to prevent artifacts such as rings in image reconstruction. This is because, if a grid pattern cannot be completely removed by the grid pattern removing unit, ring artifacts occur. This embodiment is described on the assumption that grids are inserted in both the slice direction and the CH direction. It, however, should be noted that scattered radiation is preferably removed by inserting a grid in only the slice direction. In this case, the grid in the slice direction may cause moire (beat), and the grid pattern removing unit removes moire in the slice direction. When lattice-like grids are to be used, the respective grids are preferably arranged parallel to the line of the detection elements.

Data from the X-ray sensor 101 is A/D-converted and received by a data acquisition unit (not shown). Each of FPDs constituting the X-ray sensor 101 is formed by a scintillator and a two-dimensional array of photoelectric conversion elements. Note that the photoelectric conversion elements and an amplifier system have offsets, and hence offset components are removed by an offset correction unit 310. Offset correction is performed by using, for example, the correction data generated on the basis of an output signal from the X-ray sensor 101 which is obtained without X-ray irradiation. The image offset-corrected by the offset correction unit 310 is stored in an image storage unit 305.

Reconstruction of an image will be described below, which is performed upon removing the influence of the grid 102 by performing image processing with respect to the image stored in the image storage unit 305. A processing sequence in the first embodiment will be described with reference to the flow chart of FIG. 4.

Two kinds of images are basically obtained by the X-ray sensor 101. One is a gain image for gain correction, and the other is an image obtained by imaging a subject to be examined. A gain image is an image acquired in a state wherein nothing is placed in the reconstruction area 106 or a homogeneous material or cylindrical water phantom is placed in the area. This image is stored in the image storage unit 305 (step S101). When a water phantom is used, water correction can be done simultaneously with gain correction. A gain image is generally acquired before a subject image is acquired, but may be acquired after a subject image is acquired. That is, if the S/N ratio of a reconstructed image is determined to be lower than a predetermined reference, a gain image may be acquired again to perform correction again.

The subject is then placed in the reconstruction area 106 and imaged to obtain a subject image (step S102). This subject image is also stored in the image storage unit 305. Since grid shadows are cast on both the above stored subject image and gain image, the grid shadows are canceled at the same time a dividing unit 306 performs division processing to perform gain correction (step S103). In this processing, the gain image is applied to the subject image to perform gain correction. The image may be log-transformed to be subtracted from each other.

In order to reduce the grid shadow remaining after division, the X-ray imaging conditions (mainly tube voltage) for a gain image are preferably matched with those for a subject image. That is, a plurality of gain images are preferably prepared in accordance with X-ray conditions, and a gain image obtained under conditions similar to the imaging conditions is preferably used. One of the methods of realizing this is to match the X-ray conditions set in step S101 with those in step S102.

It is, however, empirically difficult to completely remove a grid shadow by the above division. As a result, a ring-like artifact occurs. In order to remove the remaining grid shadow, grid pattern removal processing is executed by a grid pattern removing unit 304 (step S104). Algorithms for grid removal include a method using a filter and a method of predicting and subtracting a grid pattern.

According to the method using a filter, since the spatial frequency of a grid pattern is known, a filter designed to reduce the spectrum of the frequency is used. This method will be described with reference to FIGS. 7A and 7B. FIG. 7A schematically shows the state of an one-dimensional amplitude spectrum in a direction perpendicular to the grid pattern of an image. Referring to FIG. 7A, reference numeral 32 denotes the spectrum of an image component; 31, the spectrum of a grid pattern component, and more specifically, a substantial spectrum shape without consideration of noise. FIG. 7B schematically shows the state of a spectrum after grid removal filtering. Referring to FIG. 7B, reference numeral 33 denotes the characteristic of the filter used; and 34, an image spectrum after filtering.

According to the method of predicting and subtracting a grid pattern, an image is scanned with a proper number of pixels in a direction perpendicular to the grid pattern to detect the frequency of the pattern within the corresponding interval. A grid pattern equal in frequency and amplitude to the detected grid pattern is formed by a sine waveform, which in turn is subtracted from the image (for an algorithm for predicting a grid pattern, see the description made with reference to FIGS. 18 and 19 in Japanese Patent Laid-Open No. 2002-325765).

In using either the method using a filter or the method of predicting and subtracting a grid pattern, a grid is preferably observed as a grid pattern in the form of a stable sine wave with little beat (amplitude fluctuation) caused by sampling. According to Japanese Patent Laid-Open No. 2001-212139, the relation between a spatial frequency fg of a grid and a sampling frequency fs is set to satisfy fg$\leq$0.4×fs as a condition that makes it difficult to observe such a beat component. In addition, according to Japanese Patent Laid-Open No. 2001-212139, the sampling frequency fs is generally set such that the maximum frequency of a subject image becomes 30% or less of the sampling frequency, and the grid frequency fg is set to be higher than the maximum frequency of the subject image (fg$\geq$0.3×fs) to prevent the grid frequency from influencing the subject image. In this embodiment, therefore, the grid frequency is preferably set to fs (n+0.3) to fs(n+0.4) (n is a natural number) or fs (n+0.6) to fs (n+0.8) [cyc/mm].

The image subjected to grid pattern removal processing and gain correction in this manner is transferred to a reconstruction unit 307, which in turn reconstructs a tomogram or three-dimensional image (step S105). The reconstructed image is displayed by the image display unit 308 (step S106). Note that the output form of an image is not limited to outputting to the display device. For example, the image can be printed out on a film.

The above flow of processing from data acquisition to image output operation is managed and executed by a system control unit 301. Note that mechanical rotation and the like in data acquisition are controlled by a mechanical control unit 302. Instructions from the operator, e.g., as an instruction to start imaging, are input through an user interface unit 303.

As described above, according to the first embodiment, in the cone beam CT device using the FPDs, scattered radiation can be effectively removed by the grid, and damage to an image due to the grid can be effectively reduced, thereby implementing image reconstruction with high image quality.

<Second Embodiment>

The second embodiment will be described next. The arrangement and the like of a cone beam CT device are the same as those in the first embodiment.

Figure 5:
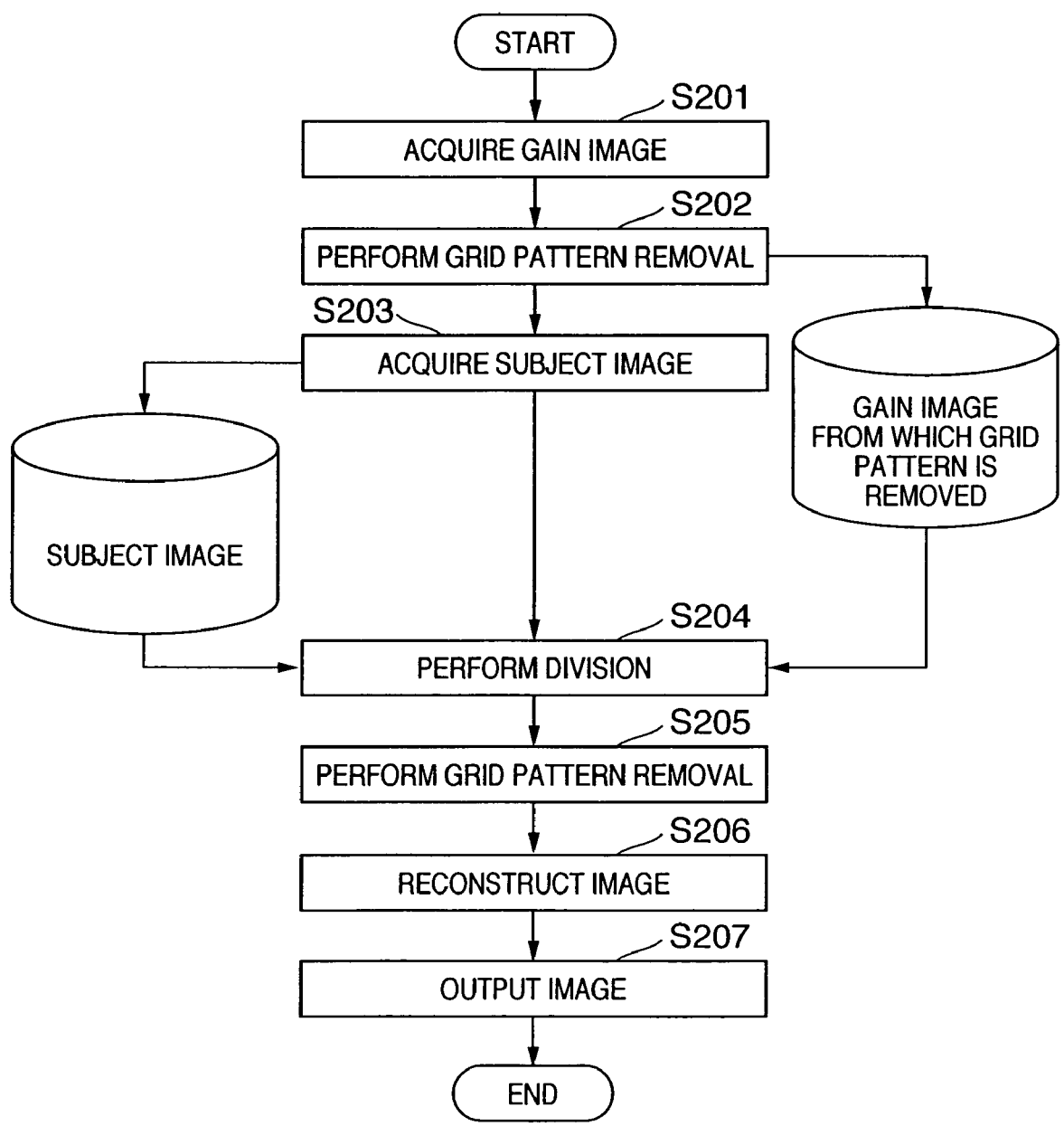
FIG. 5 is a flow chart for explaining imaging processing by a cone beam CT device according to the second embodiment.

FIG. 5 is a flow chart for explaining imaging processing in the second embodiment. When a gain image is obtained by imaging, an offset correction unit 310 performs offset processing of the image. The resultant gain image is then subjected to grid pattern removal processing described in step S104 (steps S201 and S202). The gain image from which the grid pattern is removed in this manner is stored in the image storage unit 305.

A subject image is then acquired, and the offset of the image is corrected by the offset correction unit 310 (step S203). A dividing unit 306 applies division based on the gain image, from which the grid pattern is removed, to the subject image (the images may be LOG-transformed to be subtracted from each other), thereby performing gain correction (step S204). Since a grid pattern remains in the gain-corrected subject image, grid pattern removable processing similar to that in step S104 in the first embodiment is performed (step S205).

The image having undergone grid pattern removal and gain correction in the above manner is transferred to a reconstruction unit 307 to be reconstructed into a tomogram or three-dimensional image (step S206). The reconstructed image is displayed on an image display unit 308 (step S207). Note that the output form of an image is not limited to outputting to the display device. For example, the image can be printed out on a film.

The grid pattern to be subjected to grid pattern processing in the first embodiment is mostly canceled by gain correction, and hence has a very small spectrum. In contrast to this, the spectrum of the grid pattern in the second embodiment is strong. It is therefore necessary to change the threshold for grid pattern detection.

<Third Embodiment>

The third embodiment will be described next. The arrangement and the like of a cone beam CT device are the same as those in the first embodiment.

Figure 6:
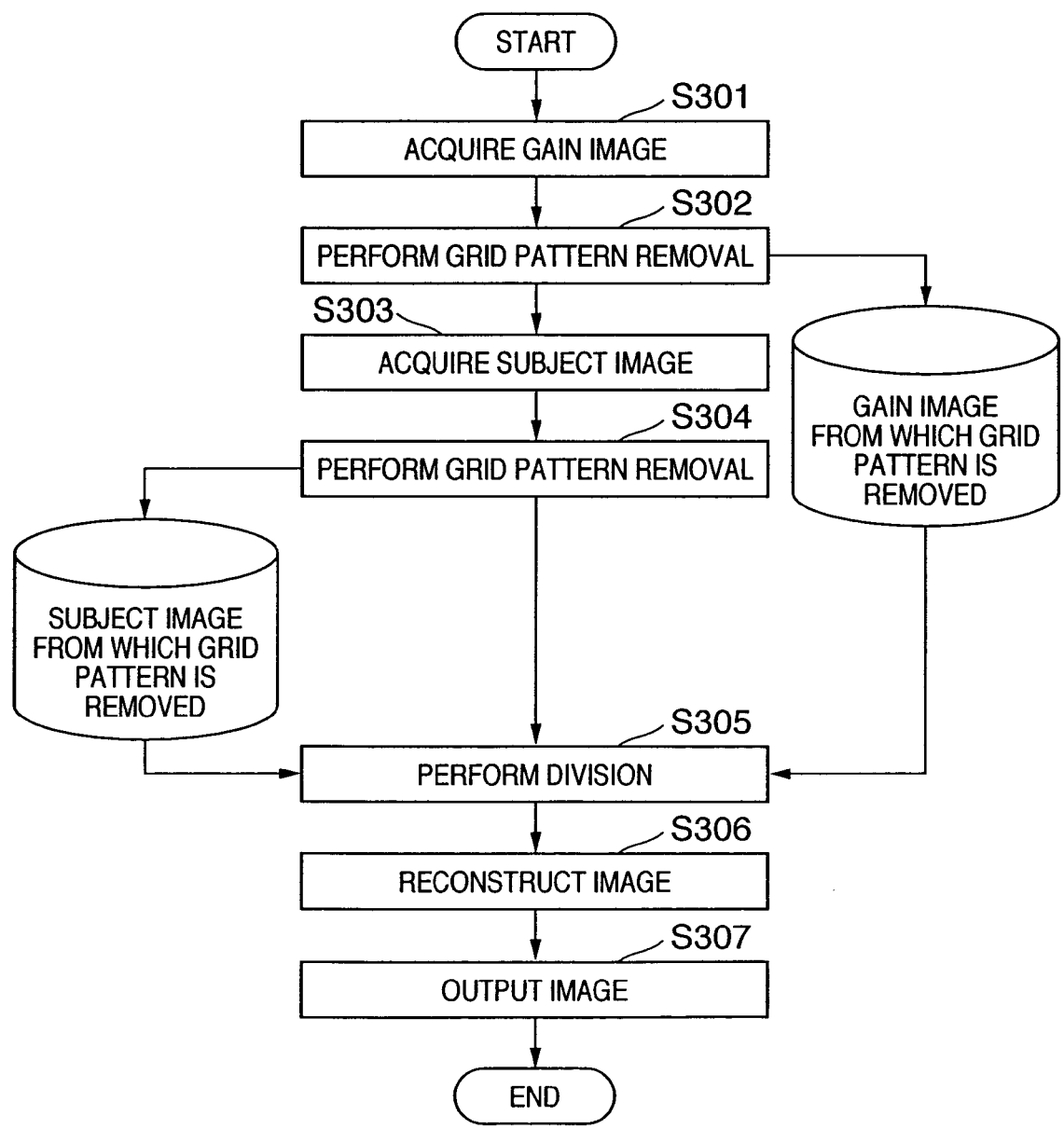
FIG. 6 is a flow chart for explaining imaging processing by a cone beam CT device according to the third embodiment.

FIG. 6 is a flow chart for explaining imaging processing in the third embodiment. In the third embodiment, grid pattern removal processing is applied in advance to both the gain image and the subject image obtained by imaging to eliminate (or reduce) grid patterns, and then the resultant images are subjected to division, thereby implementing gain correction and grid pattern removal.

Referring to FIG. 6, when a gain image is obtained by imaging, the image is subjected to offset processing in an offset correction unit 310, and the resultant gain image is subjected to the grid pattern removal processing described in step S104 (steps S301 and S302). The gain image from which a grid pattern is removed in this manner is stored in an image storage unit 305.

When a subject image is acquired, the offset of the image is corrected by the offset correction unit 310, and the resultant subject image is subjected to the grid pattern removal processing described in step S104 (steps S303 and S304). The subject image from which a grid pattern is removed in this manner is stored in the image storage unit 305.

A dividing unit 306 then performs division based on the gain image, from which the grid pattern is removed, to the subject image (the images may be LOG-transformed to be subtracted from each other), thereby performing gain correction (step S305).

The image subjected to grid pattern removal and gain correction in the above manner is transferred to the reconstruction unit 307 to be reconstructed into a tomogram or three-dimensional image (step S306). The reconstructed image is displayed on an image display unit 308 (step S307). Note that the output form of an image is not limited to outputting to the display device. For example, the image can be printed out on a film.

As described above, according to the third embodiment, after grid pattern removal processing is performed with respect to both a gain image and an acquired image, gain correction is performed.

<Fourth Embodiment>

The fourth embodiment will be described next. The arrangement and the like of a cone beam CT device are the same as those in the first embodiment.

Imaging processing in the fourth embodiment will be described with reference to the flow chart of FIG. 4 as in the first embodiment. In the fourth embodiment, a gain image is obtained by imaging without inserting a grid. No grid pattern is cast on a gain image. A subject image is obtained by imaging upon insertion of a grid. Gain correction is performed by division processing in step S103. A grid pattern is cast on the gain-corrected image at contrast similar to that on the subject image. Grid pattern removal processing in step S104 is applied to the gain-corrected image to implement grid pattern removal.

Figure 4:
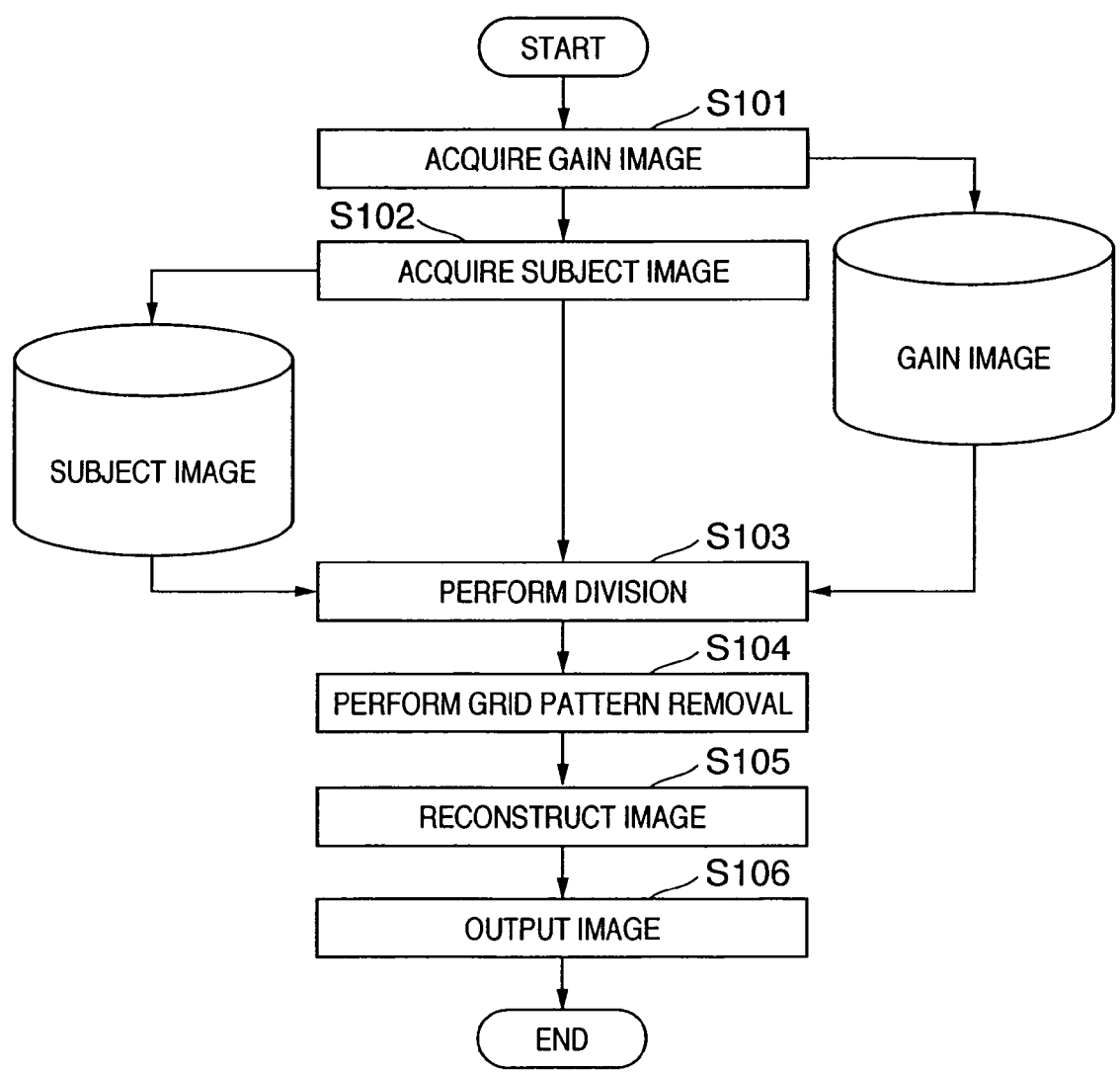
FIG. 4 is a flow chart for explaining imaging processing by the cone beam CT device according to the first embodiment.

Referring to FIG. 4, when a gain image is obtained by imaging, the image is stored in an image storage unit 305 upon offset processing by an offset correction unit 310 (step S101).

When a subject image is acquired (step S102), the offset of the image is corrected by the offset correction unit 310, and the gain image acquired in step S101 is gain-corrected (step S103). Thereafter, the grid pattern removal processing described in step S104 is performed with respect to the gain-corrected image. The subject image from which the grid pattern is removed is stored in the image storage unit 305.

The image subjected to gain correction and grid pattern removal in the above manner is transferred to a reconstruction unit 307 to reconstruct a tomogram or three-dimensional image (step S105). The reconstructed image is displayed on an image display unit 308 (step S106). Note that the output form of an image is not limited to outputting to the display device. For example, the image can be printed out on a film.

As described above, according to the fourth embodiment, grid pattern removal is applied to only an image after gain correction.

As has been described above, according to each of the above embodiments, in the cone beam CT device using the FPDs, since scattered radiation can be removed by using the grid, and a grid pattern can be properly removed without reciprocating the grid, a reconstructed image can be obtained which exhibits high tissue contrast in a slice image without any ring-like virtual image. In each of the embodiments shown in FIGS. 1 and 3, the two-dimensional detector is placed in an almost arcuated shape. However, the overall detector may be placed flat. If the overall detector is placed flat, a grid can be formed to have one flat surface. A merit in placing the detector in an arcuated shape is that the size of the gantry can be reduced.

The following are the differences between the effects obtained by the different processes in the respective embodiments.

First of all, the first embodiment (FIG. 4) is effective if grid position precision is high when a gain image and subject image are obtained by imaging. In this case, since many grid pattern elements are removed by division (gain correction), there is no need to extremely decrease signals at the filter frequency in filter processing.

The second embodiment (FIG. 5) is effective when grid position precision is poor in obtaining a gain image and subject image by imaging. However, even with regard to a homogeneous image like a gain image, it is sometimes difficult to remove a grid pattern from an image without gain correction.

The third embodiment (FIG. 6) is also effective when grid position precision is poor in obtaining a gain image and subject image by imaging. As described above, however, even with regard to a homogeneous image like a gain image, it may sometimes be difficult to remove a grid pattern from an image without gain correction. In addition, since it is sometimes even harder to remove a grid pattern from a subject image without gain correction, processing may become more difficult than the sequence in the second embodiment.

In the fourth embodiment as well, there is no need to give consideration to grid position precision in obtaining a gain image and subject image by imaging. Furthermore, there is no need to perform the processing of removing a grid pattern from a gain image (i.e., there is no need to perform the processing of removing a grid pattern from an image without gain correction). On the other hand, the grid must be removed when a gain image is to be obtained by imaging.

Each correction processing in the first to third embodiments has been described as a means. When, however, each image processing portion is implemented by a computer, each correction processing can be implemented by software.

The object of the present invention is realized even by supplying a storage medium storing software program codes for realizing the functions of the above-described embodiments to a system or apparatus, and causing the computer (or the CPU or MPU) of the system or apparatus to read out and execute the program codes stored in the storage medium.

In this case, the program codes read out from the storage medium realize the functions of the above-described embodiments by themselves, and the storage medium storing the program codes constitutes the present invention.

As a storage medium for supplying the program codes, a flexible disk, hard disk, optical disk, magnetooptical disk, CD-ROM, CD-R, magnetic tape, nonvolatile memory card, ROM, or the like can be used.

The functions of the above-described embodiments are realized not only when the readout program codes are executed by the computer but also when the OS (Operating System) running on the computer performs part or all of actual processing on the basis of the instructions of the program codes.

The functions of the above-described embodiments are also realized when the program codes read out from the storage medium are written in the memory of a function expansion board inserted into the computer or a function expansion unit connected to the computer, and the CPU of the function expansion board or function expansion unit performs part or all of actual processing on the basis of the instructions of the program codes.

As has been described above, the present invention can effectively suppress the occurrence of artifacts in CT imaging while having an arrangement for removing scattered radiation by using a grid fixed to a radiation detector.

As many apparently widely different embodiments of the present invention can be made without departing from the spirit and scope thereof, it is to be understood that the invention is not limited to the specific embodiments thereof except as defined in the appended claims.

What is claimed is:

1. An X-ray Computed Tomography device comprising:
   an X-ray source which irradiates a subject with X-rays;
   a two-dimensional detector in which a plurality of detection elements for detecting X-rays from said X-ray source are two-dimensionally arranged;
   a rotation unit configured to relatively rotate said X-ray source and said two-dimensional detector around the subject;
   a grid which is placed in front of said two-dimensional detector to remove scattered radiation of the X-rays, said grid being detachable;
   a correction unit configured to perform computation with respect to a subject image obtained by said two-dimensional detector by using the subject image and a gain image obtained by said two-dimensional detector;
   an image processing unit configured to execute a grid pattern removal processing on the subject image corrected by said correction means; and
   a reconstruction unit configured to reconstruct an image on the basis of the subject image obtained by said image processing unit,
   wherein said grid forms stripes using a plurality of grid plates, and each of the plurality of grid plates is placed substantially parallel to a plane of rotation of said X-ray source, and
   the gain image is obtained while said grid is detached.

2. The device according to claim 1, wherein each of the plurality of grid plates is placed so as to focus on said X-ray source.

3. The device according to claim 1, wherein letting fg be a spatial frequency of the plurality of grid plates of said grid, fs be a spatial frequency of sampling of said two-dimensional detector, and n be a natural number, fg is represented by fs (n+0.3) to fs (n+0.4) or fs (n+0.6) to fs (n+0.8) [cyc/mm].

4. An image processing method in a X-ray Computed Tomography device including an X-ray source which irradiates a subject with X-rays, a two-dimensional detector in which a plurality of detection elements for detecting X-rays from the X-ray source are two-dimensionally arranged, a rotation unit configured to relatively rotate said X-ray source and said two-dimensional detector around the subject, and a grid which is placed in front of the two-dimensional detector to remove scattered radiation of the X-rays, said grid being detachable, comprising:
   a correction step of performing computation with respect to a subject image obtained by the two-dimensional detector by using the subject image and a gain image obtained by the two-dimensional detector;
   an image processing step of executing a grid pattern removal processing on the subject image corrected by said correction step; and
   a reconstruction step of reconstructing an image on the basis of the subject image obtained in the image processing step,
   wherein said grid forms stripes using a plurality of grid plates, and each of the plurality of grid plates is placed substantially parallel to a plane of rotation of said X-ray source, and the gain image is obtained while said grid is detached.

5. The method according to claim 4, wherein each of the plurality of grid plates is placed so as to focus on the X-ray source.

6. The method according to claim 4, wherein letting fg be a spatial frequency of the plurality of grid plates of the grid, fs be a spatial frequency of sampling of the two-dimensional detector, and n be a natural number, fg is represented by fs (n+0.3) to fs (n+0.4) or fs (n+0.6) to fs (n+0.8) [cyc/mm].

7. An X-ray Computed Tomography device comprising:
an X-ray source which irradiates a subject with X-rays;
a two-dimensional detector in which a plurality of detection elements for detecting X-rays from said X-ray source are two-dimensionally arranged;
a rotation unit configured to relatively rotate said X-ray source and said two-dimensional detector around the subject;
a grid which is placed in front of said two-dimensional detector to remove scattered radiation of the radiation;
a correction unit configured to perform computation with respect to a subject image obtained by said two-dimensional detector by using the subject image and a gain image obtained by said two-dimensional detector;
an image processing unit configured to execute a grid pattern removal processing on the subject image corrected by said correction means; and
a reconstruction unit configured to reconstruct an image on the basis of the subject image obtained by said image processing unit,
wherein said grid forms stripes using a plurality of grid plates, and each of the plurality of grid plates is placed substantially parallel to a plane of rotation of said X-ray source, and the gain image is obtained by performing grid removal processing to remove a grid pattern due to said grid with respect to a gain image obtained by said two-dimensional detector.

8. A imaging processing method in an X-ray Computed Tomography device including an X-ray source which irradiates a subject with X-rays, a two-dimensional detector in which a plurality of detection elements for detecting X-ray from said X-ray source are two-dimensionally arranged, a rotation unit configured to relatively rotate said X-ray source and said two-dimensional detector around the subject and a grid which is placed in front of said two-dimensional detector to remove scattered radiation of the radiation, comprising:
a correction step of performing computation with respect to a subject image obtained by said two-dimensional detector by using the subject image and a gain image obtained by said two-dimensional detector;
an image processing step of executing a grid pattern removal processing on the subject image corrected by said correction step; and
a reconstruction step of reconstructing an image on the basis of the subject image obtained by said image processing step,
wherein said grid forms stripes using a plurality of grid plates, and each of the plurality of grid plates is placed substantially parallel to a plane of rotation of said X-ray source, and the gain image is obtained by performing grid removal processing to remove a grid pattern due to said grid with respect to a gain image obtained by said two-dimensional detector.

* * * * *